United States Patent [19]
Chang et al.

[11] Patent Number: 5,824,529
[45] Date of Patent: Oct. 20, 1998

[54] METHOD FOR CLONING AND PRODUCING THE PSHAI RESTRICTION ENDONUCLEASE

[75] Inventors: Zhiyuh Chang, Beverly; Richard D. Morgan, Middleton, both of Mass.

[73] Assignee: New England Biolabs, Inc., Beverly, Mass.

[21] Appl. No.: 611,510

[22] Filed: Mar. 6, 1996

[51] Int. Cl.⁶ .............................. C12N 9/22; C12N 15/55
[52] U.S. Cl. ................ 435/199; 435/320.1; 435/252.33; 536/23.2
[58] Field of Search .............................. 435/199, 320.1, 435/252.33; 536/23.2

[56] References Cited

U.S. PATENT DOCUMENTS

Re. 35,248  5/1996  Benner et al. ....................... 435/172.3
5,200,333   4/1993  Wilson ................................ 435/172.3

FOREIGN PATENT DOCUMENTS 0 193 413  12/1993  European Pat. Off. .

OTHER PUBLICATIONS

Kosykh, et al., Molec. Gen. Genet., 178:717–719 (1980).
Mann, et al., Gene, 3:97–112 (1978).
Walder, et al., Proc. Nat. Acad. Sci., 78:1503–1507 (1981).
Bougueleret, et al., Nucl. Acid Res., 12:3659–3676 (1984).
Gingeras and Brooks, Proc. Natl. Acad. Sci. USA 80:402–406 (1983).
Theriault and Roy, Gene, 19:355–359 (1982).
Blumenthal, et al., J. Bacteriol., 164:501–509 (1985).
Kiss, et al., Nucl. Acid Res., 13:6403–6421 (1985).
Szomolanyi, et al, Gene, 10:219–225 (1980).
Janulaitis, et al., Gene, 20:197–204 (1982).
Kiss and Baldauf, Gene, 21:111–119 (1983).
Walder, et al., (J. Biol. Chem., 258:1235–1241 (1983).
Piekarowicz, et al., Nucleic Acid Res. 19:1831–1835 (1991).
Piekarowicz, et al., J. Bacteriology, 173:150–155 (1991).
Fomenkov, et al., Nucleic Acids Res. 22:2399–2403 (1994).
Lunnen, et al., Gene, 74:25–32 (1988).
Raleigh and Wilson, Proc. Natl. Acad. Sci, USA, 83:9070–9074 (1986).
Heitman and Model, J. Bact., 196:3243–3250 (1987).
Raleigh, et al., Genetics, 122:279–296 (1989).
Waite–Rees, et al., J. Bacteriology, 173:5207–5219 (1991).
Wilson, Methods in Enzymology, 216:259–279 (1992).
Ochman, et al., Genetics, 120:621 (1988).
Triglia, et al., Nucl. Acids Res. 16:8186 (1988).
Silver and Keerikatte, J. Cell Biochem., (Suppl.) 13E:306, Abstract No. WH239 (1989).
Brooks, et al. Nucleic Acid Res. 17:979–997 (1989).
Fuller, Gene, 19:43–54 (1982).
Shimatake and Rosenberg, Nature, 292:128 (1981).
Shine & Dalgarno, Proc. Natl. Acad. Sci. USA, 71:1342–1346 (1974).
Ikemura, J. Mol. Biol., 151:389–409 (1981).
Miyahara, M., et. al. (1990) Gene 87, 119–122.
Lunnen, K. D, et. al. (1988) Gene 74, 25–32.

*Primary Examiner*—Charles L. Patterson, Jr.
*Attorney, Agent, or Firm*—Gregory D. Williams

[57] ABSTRACT

The present invention is directed to a method for cloning and producing the PshAI restriction endonuclease by (1) introducing the restriction endonuclease gene from *Plesiomonas shigelloides* into a host whereby the restriction gene is expressed; (2) fermenting the host which contains the vector encoding and expressing the PshAI restriction endonuclease activity, and (3) purifying the PshAI restriction endonuclease from the fermented host which contains the vector encoding and expressing the PshAI restriction endonuclease activity.

7 Claims, 3 Drawing Sheets

The DNA of *Plesiomonas shigelloides* is purified.
↓
The *Psh*AI restriction endonuclease protein is partially purified.
↓
A selectable vector, pUC19PshAI, containing 3 *Psh*AI sites is constructed and libraries of *Plesiomonas shigelloides* DNA are made in this vector.
↓
Methylase clones are selected and identified by the methylase selection method.
↓
The DNA sequence of one of the methylase clone is determined and the location and the orientation of the *Psh*AI methylase gene is determined.
↓
The *Psh*AI restriction endonuclease protein is purified to homogeneity.
↓
Amino acid sequence at the *Psh*AI endonuclease N-terminus is determined.
↓
A 2.9 kb *Avr*II fragment containing 2.1 kb of DNA sequences 5' to the methylase clone is identified by Southern hybridization.
↓
The DNA of this 2.9 kb *Avr*II fragment is amplified by inverse PCR method
↓
Fragments of the 2.9 kb inverse PCR product are cloned into pUC19 and their DNA sequenced
↓
The *Psh*AI endonuclease gene and control gene are identified
↓
The *Psh*AI endonuclease is expressed by amplifying the *Psh*AI endonuclease gene from *Plesiomonas shigelloides* DNA and ligating the gene into an expression vector under the control of a regulated promoter.
↓
The *Psh*AI endonuclease clone is grown in a fermenter in L-broth with the appropriate antibiotic selection and induction.
↓
The *Psh*AI endonuclease is purified from the overexpressing clone p*Psh*AIRI by protein purification techniques

FIG. 1

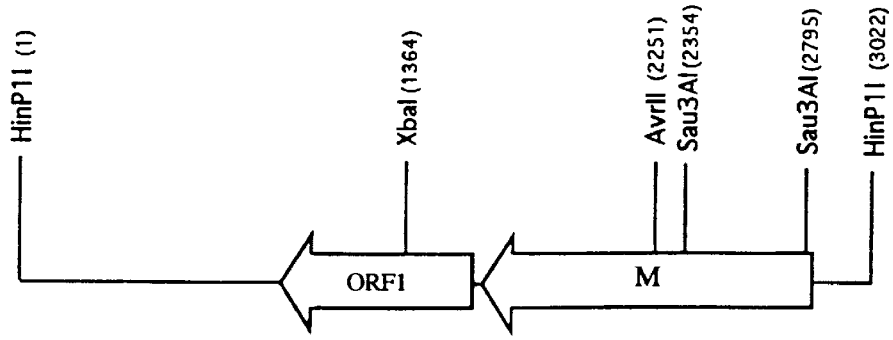
pPshAIM19 cloned DNA
FIG. 2
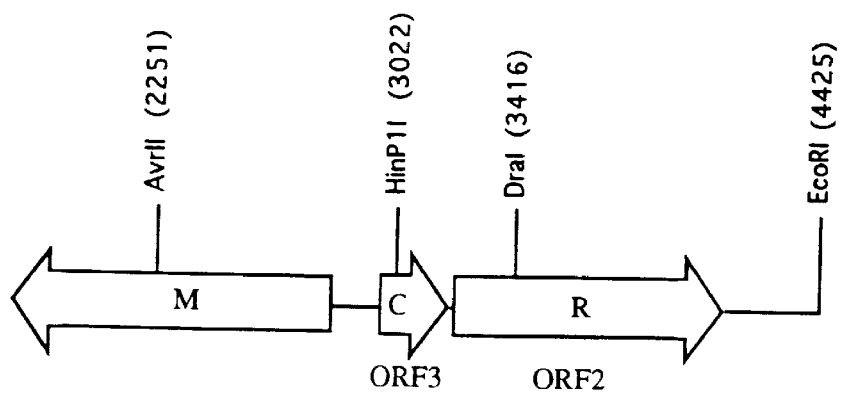
PshAI Restriction-Modification System
FIG. 3
```
PshAI                                      V K T I H D H S Y V E
EcoRV    M P K K P I L G Y P I L G C I I Y K K N D G K S M S
PshAI    L L A N L R R E R I A N S I S Q T E L S Q K L S K P
EcoRV    V R E I I K K N R V I C K L S Q G E V A K A L G K P
PshAI    Q S F I S K I E C G E R R L D V I E L L N I C A I L
EcoRV    Q S Y I S K I E Q G E R R V D V D E F I A I C F R I
PshAI    G V K F R D V V P K E Y R E L L
EcoRV    G I D P I N T L K E V I M E K K H E S S F
```
FIG. 4

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
  ( A ) LENGTH: 6 base pairs
  ( B ) TYPE: nucleic acid
  ( C ) STRANDEDNESS: double
  ( D ) TOPOLOGY: unknown ( i i ) MOLECULE TYPE: DNA ( x i ) SEQUENCE DESCRIPTION: SEQ ID NO:1:

```
        T T T A A A                                                                    6
```

( 2 ) INFORMATION FOR SEQ ID NO:2:

( i ) SEQUENCE CHARACTERISTICS:
        ( A ) LENGTH: 7 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:2:

```
        R G G N C C Y                                                                  7
```

( 2 ) INFORMATION FOR SEQ ID NO:3:

( i ) SEQUENCE CHARACTERISTICS:
        ( A ) LENGTH: 9 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:3:

```
        C A C N N N G T G                                                              9
```

( 2 ) INFORMATION FOR SEQ ID NO:4:

( i ) SEQUENCE CHARACTERISTICS:
        ( A ) LENGTH: 6 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:4:

```
        G A A T T C                                                                    6
```

( 2 ) INFORMATION FOR SEQ ID NO:5:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:5:

```
        G A C N N N N G T C                                                           1 0
```

( 2 ) INFORMATION FOR SEQ ID NO:6:

( i ) SEQUENCE CHARACTERISTICS:
        ( A ) LENGTH: 79 amino acids
        ( B ) TYPE: amino acid
        ( C ) STRANDEDNESS: Not Applicable
        ( D ) TOPOLOGY: unknown ( i i ) MOLECULE TYPE: protein ( x i ) SEQUENCE DESCRIPTION: SEQ ID NO:6:

```
        Val  Lys  Thr  Ile  His  Asp  His  Ser  Tyr  Val  Glu  Leu  Leu  Ala  Asn  Leu
        1                   5                        1 0                      1 5

Arg  Arg  Glu  Arg  Ile  Ala  Asn  Ser  Ile  Ser  Gln  Thr  Glu  Leu  Ser  Gln
```

|   |   |   |   |   | 20 |   |   |   |   | 25 |   |   |   |   | 30 |
|---|---|---|---|---|---|---|---|---|---|---|---|---|---|---|---|

Lys Leu Ser Lys Pro Gln Ser Phe Ile Ser Lys Ile Glu Cys Gly Glu
        35                  40                  45

Arg Arg Leu Asp Val Ile Glu Leu Leu Asn Ile Cys Ala Ile Leu Gly
    50                      55                      60

Val Lys Phe Arg Asp Val Val Pro Lys Glu Tyr Arg Glu Leu Leu
65                  70                    75

( 2 ) INFORMATION FOR SEQ ID NO:7:

( i ) SEQUENCE CHARACTERISTICS:
        ( A ) LENGTH: 99 amino acids
        ( B ) TYPE: amino acid
        ( C ) STRANDEDNESS: Not Applicable
        ( D ) TOPOLOGY: unknown ( i i ) MOLECULE TYPE: protein ( x i ) SEQUENCE DESCRIPTION: SEQ ID NO:7:

Met Pro Lys Lys Pro Ile Leu Gly Tyr Pro Ile Leu Gly Cys Ile Ile
1               5                    10                  15

Tyr Lys Lys Asn Asp Gly Lys Ser Met Ser Val Arg Glu Ile Ile Lys
        20                  25                  30

Lys Asn Arg Val Ile Cys Lys Leu Ser Gln Gly Glu Val Ala Lys Ala
        35                  40                  45

Leu Gly Lys Pro Gln Ser Tyr Ile Ser Lys Ile Glu Gln Gly Glu Arg
    50                      55                  60

Arg Val Asp Val Asp Glu Phe Ile Ala Ile Cys Phe Arg Ile Gly Ile
65                  70                    75                  80

Asp Pro Ile Asn Thr Leu Lys Glu Val Ile Met Glu Lys Lys His Glu
              85                    90                  95

Ser Ser Phe ( 2 ) INFORMATION FOR SEQ ID NO:8:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: unknown ( i i ) MOLECULE TYPE: DNA (synthetic)

( x i ) SEQUENCE DESCRIPTION: SEQ ID NO:8:

GACGGCCGTC                                                    10

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:9:

GGACAGTTTT  TCACTCCA                                      18

( 2 ) INFORMATION FOR SEQ ID NO:10:

( i ) SEQUENCE CHARACTERISTICS:
        ( A ) LENGTH: 33 base pairs
        ( B ) TYPE: nucleic acid ( C ) STRANDEDNESS: double
( D ) TOPOLOGY: unknown ( i i ) MOLECULE TYPE: DNA (genomic)

( x i ) SEQUENCE DESCRIPTION: SEQ ID NO:10:

TTAGATCCAG CATGCGGCTC AGGAGGCTTT CTT                33

( 2 ) INFORMATION FOR SEQ ID NO:11:

( i ) SEQUENCE CHARACTERISTICS:
( A ) LENGTH: 6 amino acids
( B ) TYPE: amino acid
( C ) STRANDEDNESS: Not Applicable
( D ) TOPOLOGY: unknown ( i i ) MOLECULE TYPE: protein ( x i ) SEQUENCE DESCRIPTION: SEQ ID NO:11:

Gly Gln Phe Phe Thr Pro
1                 5

( 2 ) INFORMATION FOR SEQ ID NO:12:

( i ) SEQUENCE CHARACTERISTICS:
( A ) LENGTH: 11 amino acids
( B ) TYPE: amino acid
( C ) STRANDEDNESS: Not Applicable
( D ) TOPOLOGY: unknown ( i i ) MOLECULE TYPE: protein ( x i ) SEQUENCE DESCRIPTION: SEQ ID NO:12:

Leu Asp Pro Ala Cys Gly Ser Gly Gly Phe Leu
1                 5                    10

( 2 ) INFORMATION FOR SEQ ID NO:13:

( i ) SEQUENCE CHARACTERISTICS:
( A ) LENGTH: 27 base pairs
( B ) TYPE: nucleic acid
( C ) STRANDEDNESS: double
( D ) TOPOLOGY: unknown ( i i ) MOLECULE TYPE: DNA (genomic)

( x i ) SEQUENCE DESCRIPTION: SEQ ID NO:13:

GATGCGATAC TCACAAACCC TCCGTTT                       27

( 2 ) INFORMATION FOR SEQ ID NO:14:

( i ) SEQUENCE CHARACTERISTICS:
( A ) LENGTH: 9 amino acids
( B ) TYPE: amino acid
( C ) STRANDEDNESS: Not Applicable
( D ) TOPOLOGY: unknown ( i i ) MOLECULE TYPE: protein ( x i ) SEQUENCE DESCRIPTION: SEQ ID NO:14:

Asp Ala Ile Leu Thr Asn Pro Pro Phe
1                 5

( 2 ) INFORMATION FOR SEQ ID NO:15:

( i ) SEQUENCE CHARACTERISTICS:
( A ) LENGTH: 6 base pairs
( B ) TYPE: nucleic acid
( C ) STRANDEDNESS: double
( D ) TOPOLOGY: unknown (ii) MOLECULE TYPE: DNA (genomic)

(xi) SEQUENCE DESCRIPTION: SEQ ID NO:15:

GGAGAG 6

(2) INFORMATION FOR SEQ ID NO:16:

(i) SEQUENCE CHARACTERISTICS:
(A) LENGTH: 28 amino acids
(B) TYPE: amino acid
(C) STRANDEDNESS: Not Applicable
(D) TOPOLOGY: unknown (ii) MOLECULE TYPE: protein (xi) SEQUENCE DESCRIPTION: SEQ ID NO:16:

Met Ser Ile Leu Asp Asn Glu Lys Gln Leu Xaa Ile Leu Asn Ile Ile
1               5                   10                  15
Asn Glu Gly Val Thr Pro Ala Ile Ile Pro Glu Leu
            20                  25

(2) INFORMATION FOR SEQ ID NO:17:

(i) SEQUENCE CHARACTERISTICS:
(A) LENGTH: 25 base pairs
(B) TYPE: nucleic acid
(C) STRANDEDNESS: single
(D) TOPOLOGY: unknown (ii) MOLECULE TYPE: DNA (synthetic)

(xi) SEQUENCE DESCRIPTION: SEQ ID NO:17:

GAGGGGTAGT TTCTGAGTGA AGACC 25

(2) INFORMATION FOR SEQ ID NO:18:

(i) SEQUENCE CHARACTERISTICS:
(A) LENGTH: 24 base pairs
(B) TYPE: nucleic acid
(C) STRANDEDNESS: single
(D) TOPOLOGY: unknown (ii) MOLECULE TYPE: DNA (synthetic)

(xi) SEQUENCE DESCRIPTION: SEQ ID NO:18:

AATACGTTAT CACTATAAAT ATCC 24

(2) INFORMATION FOR SEQ ID NO:19:

(i) SEQUENCE CHARACTERISTICS:
(A) LENGTH: 47 base pairs
(B) TYPE: nucleic acid
(C) STRANDEDNESS: single
(D) TOPOLOGY: unknown (ii) MOLECULE TYPE: DNA (synthetic)

(xi) SEQUENCE DESCRIPTION: SEQ ID NO:19:

GAGACTGCAG GAGGTAATTA ATATGTCCAT TTAGATAAT GAAAAAC 47

(2) INFORMATION FOR SEQ ID NO:20:

(i) SEQUENCE CHARACTERISTICS:
(A) LENGTH: 27 base pairs
(B) TYPE: nucleic acid
(C) STRANDEDNESS: single
(D) TOPOLOGY: unknown -continued (ii) MOLECULE TYPE: DNA (synthetic)

(xi) SEQUENCE DESCRIPTION: SEQ ID NO:20:

GTAGAATTCG GATCCGGCGA ATGAGAG 27

METHOD FOR CLONING AND PRODUCING THE PSHAI RESTRICTION ENDONUCLEASE

BACKGROUND OF THE INVENTION

The present invention relates to recombinant DNA which encodes the PshAI restriction endonuclease and modification methylase, and the production of PshAI restriction endonuclease from the recombinant DNA.

Type II restriction endonucleases are a class of enzymes that occur naturally in bacteria. When they are purified away from other bacterial components, restriction endonucleases can be used in the laboratory to cleave DNA molecules into precise fragments for molecular cloning and gene characterization.

Restriction endonucleases act by recognizing and binding to particular sequences of nucleotides (the 'recognition sequence') along the DNA molecule. Once bound, they cleave the molecule within, or to one side of, the recognition sequence. Different restriction endonucleases have affinity for different recognition sequences. Over one hundred and eighty restriction endonucleases with unique specificities have been identified among the many hundreds of bacterial species that have been examined to date.

Bacteria tend to possess at most, only a small number of restriction endonucleases per species. The endonucleases typically are named according to the bacteria from which they are derived. Thus, the species *Deinococcus radiophilus* for example, synthesizes three different restriction endonucleases, named DraI, DraII and DraIII. These enzymes recognize and cleave the sequences TTTAAA (SEQ ID NO:1), PuGGNCCPy (SEQ ID NO:2) and CACNNNGTG (SEQ ID NO:3), respectively. *Escherichia coli* RY13, on the other hand, synthesizes only one enzyme, EcoRI, which recognizes the sequence GMTTC (SEQ ID NO:4).

It is thought that in nature, restriction endonucleases play a protective role in the welfare of the bacterial cell. They enable bacteria to resist infection by foreign DNA molecules like viruses and plasmids that would otherwise destroy or parasitize them. They impart resistance by cleaving invading foreign DNA molecule each time that the recognition sequence occurs. The cleavage that takes place disables many of the infecting genes and renders the DNA susceptible to further degradation by non-specific nucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify one or other of the nucleotides within the sequence by the addition of a methyl group. Following methylation, the recognition sequence is no longer cleaved by the restriction endonuclease. The DNA of a bacterial cell is always fully modified by virtue of the activity of its modification methylase. It is therefore completely insensitive to the presence of the endogenous restriction endonuclease. It is only unmodified, and therefore identifiably foreign DNA, that is sensitive to restriction endonuclease recognition and cleavage.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., *Molec. Gen. Genet* 178: 717–719, (1980); HhaII: Mann et al., *Gene* 3: 97–112, (1978); PstI: Walder et al., *Proc. Nat. Acad. Sci.* 78 1503–1507, (1981), the disclosures of which are hereby incorporated by reference herein). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acid. Res.* 12: 3659–3676, (1984); PaeR7: Gingeras and Brooks, *Proc. Natl. Acad. Sci. USA* 80: 402–406, (1983); Theriault and Roy, *Gene* 19: 355–359 (1982); PvuII: Blumenthal et al., *J. Bacteriol.* 164: 501–509, (1985), the disclosures of which are hereby incorporated by reference herein).

A third approach which is being used to clone a growing number of systems, involves selection for an active methylase gene (refer to our EPO No.: 193,413 published, Sep. 3, 1986 and BsuRI: Kiss et al., *Nucl. Acid. Res.* 13: 6403–6421, (1985), the disclosures of which are hereby incorporated by reference herein). Since restriction and modification genes are often closely linked, both genes can often be cloned simultaneously. This selection does not always yield a complete restriction system however, but instead yields only the methylase gene (BspRI: Szomolanyi et al., *Gene* 10: 219–225, (1980); Bcn I: Janulaitis et al, *Gene* 20: 197–204 (1982); Bsu RI: Kiss and Baldauf, *Gene* 21: 111–119, (1983); and Msp I: Walder et al., *J. Biol. Chem.* 258: 1235–1241, (1983), the disclosures of which are hereby incorporated by reference herein).

Another method for cloning methylase and endonuclease genes is based on a colorimetric assay for DNA damage. When screening for a methylase, the plasmid library is transformed into the host *E. coli* strain such as AP1-200. The expression of a methylase will induce the SOS response in an *E.coli* strain which is McrA+, McrBC+, or Mrr+. The AP1-200 strain is temperature sensitive for the Mcr and Mrr systems and includes a lac-Z gene fused to the damage inducible dinD locus of *E. coli*. The detection of recombinant plasmids encoding a methylase or endonuclease gene is based on induction at the restrictive temperature of the lacZ gene. Transformants encoding methylase genes are detected on LB agar plates containing X-gal as blue colonies. (Piekarowicz, et.al., *Nucleic Acids Res.* 19:1831–1835, (1991) and Piekarowicz, et. al. *J. Bacteriology* 173:150–155 (1991), the disclosures of which are hereby incorporated by reference herein). Likewise, the *E. coli* strain ER1992 contains a dinD1-Lac Z fusion but is lacking the methylation dependent restriction systems McrA, McrBC and Mrr. In this system (called the "endo-blue" method), the endonuclease gene can be detected in the abscence of it's cognate methylase when the endonuclease damages the host cell DNA, inducing the SOS response. The SOS-induced cells form deep blue colonies on LB agar plates supplemented with X-gal. (Fomenka et al. *Nucleic Acids Res.* 22:2399–2403 (1994), the disclosure of which is hereby incorporated by reference herein).

Sometimes the straight-forward methylase selection method fails to yield a methylase (and/or endonuclease) clone due to various obstacles. See, e.g., Lunnen, et al., *Gene,* 74(1):25–32 (1988), the disclosure of which is hereby incorporated by reference herein. One potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease.

Another obstacle to cloning restriction-modification systems lies in the discovery that some strains of *E. coli* react adversely to cytosine or adenine modification; they possess systems that destroy DNA containing methylated cytosine (Raleigh and Wilson, *Proc. Natl. Acad. Sci., USA* 83:9070–9074, (1986), the disclosure of which are hereby incorporated by reference herein) or methylated adenine (Heitman and Model, *J. Bact.* 196:3243–3250, (1987); Raleigh, Trimarchi, and Revel, *Genetics,* 122:279–296, (1989) Waite-Rees, et al., *J. Bacteriology,* 173:5207–5219 (1991), the disclosures of which are hereby incorporated by reference herein). Cytosine-specific or adenine-specific methylase genes cannot be cloned easily into these strains, either on their own, or together with their corresponding endonuclease genes. To avoid this problem it is necessary to use mutant strains of *E. coli* (McrA⁻ and McrB⁻ or Mrr⁻) in which these systems are defective.

A third potential difficulty is that some restriction endonuclease and methylase genes may not express in *E. coli* due to differences in the transcription machinery of the source organism and *E. coli*, such as differences in promotor and ribosome binding sites. The methylase selection technique requires that the methylase express well enough in *E. coli* to fully protect at least some of the plasmids carrying the gene.

Because purified restriction endonucleases, and to a lesser extent, modification methylases, are useful tools for characterizing genes in the laboratory, there is a commercial incentive to obtain bacterial strains through recombinant DNA techniques that synthesize these enzymes in abundance. Such strains would be useful because they would simplify the task of purification as well as providing the means for production in commercially useful amounts.

SUMMARY

The present invention relates to recombinant DNA encoding the genes for the PshAI restriction endonuclease and modification methylase obtainable from *Plesiomonas shigelloides* as well as related methods for the production of these enzymes from the recombinant DNA. This invention also relates to a transformed host which expresses the restriction endonuclease PshAI, an enzyme which recognizes the DNA sequence 5' GACNNNNGTC 3' (SEQ ID NO:5) and cleaves at the middle of the recognition sequence to produce blunt ends. PshAI restriction endonuclease produced according to the present invention is substantially pure and free of the contaminants normally found in restriction endonuclease preparations made by conventional techniques.

The PshAI methylase gene was obtained generally in accordance with the technique referred to as methylase selection (U.S. Pat. No. 5,200,333, the disclosure of which is hereby incorporated by reference herein). However none of the clones obtained by methylase selection expressed detectable PshAI restriction endonuclease activity.

The subsequent search for the restriction gene was complicated by the fact that the restriction gene is not immediately adjacent to the methylase as is the case in the majority of restriction systems. 3' of the methylase there was an open reading frame which when placed in an expression system did not produce any PshAI restriction activity, while 5' of the methylase gene there was the N-terminal part of an open reading frame which continued open off the end of the clone. (This open reading frame was subsequently found to have homology to the C (control) gene of EcoRV.)

In order to locate and positively identify the PshAI endonuclease gene the N-terminal amino acid sequence of the PshAI endonuclease protein was needed. To this end, a protein purification method was developed to purify the PshAI endonuclease to near homogeneity from *Plesiomonas shigelloides*. The purified PshAI endonuclease was used to determine the N-terminal amino acid sequence of PshAI endonuclease. This amino acid sequence was compared with amino acid translation of the DNA sequence of the methylase clones obtained from the methylase selection technique. Since no match was found, DNA contiguous to the PshAI methylase clones was amplified by inverse PCR techniques, cloned in pieces so as to not contain an intact endonuclease gene and sequenced. An open reading frame in which the deduced amino acid sequence matched the N-terminal amino acid sequence of PshAI endonuclease was located 5' of the methlase gene and separated from the methylase by a gene having homology to the EcoRV control gene. (Bougueleret, et al., supra). The PshAI endonuclease gene was then cloned into an appropriate expression vector and introduced into a host which was pre-modified with the PshAI methylase carried on a separate, compatible vector.

The preferred method for cloning the PshAI restriction-modification system consists of creating a vector containing multiple PshAI sites and cloning the PshAI methylase by methylase selection. The DNA sequence of PshAI methylase positive clones is determined. The PshAI endonuclease is purified to near homogeneity, and the amino acid sequence at the N-terminus of the protein is determined. DNA 5' to the methylase clones is amplified by inverse PCR techniques, cloned and sequenced. The PshAI endonuclease gene is identified based on the DNA sequence and amino acid sequence data. The PshAI endonuclease can then be expressed by amplifying the complete gene from *Plesiomonas shigelloides* DNA and cloning it into an expression vector such as pRRS. This construct is introduced into a host which is premodified at PshAI sites by virtue of a PshAI methylase gene carried on a separate compatible plasmid. PshAI endonuclease is produced by growing the host containing the PshAI endonuclease and methylase genes, inducing with the appropriate expression conditions, harvesting purifells and purifying the PshAI endonuclease.

BRIEF DESCRIPTION OF THE DRAWINGS

FIG. 1 illustrates the preferred method for cloning and producing the PshAI restriction endonuclease.

FIG. 2 is a restriction map of the *Plesiomonas shigelloides* DNA contained in the methylase clone pPshAIM19. This clone pPshAIM19 is obtained by methylase selection and contains a full length PshAI methylase. The location and orientation of the PshAI methylase and also ORF1 are shown.

FIG. 3 is shows the locations and orientations of the PshAI methylase gene, the control gene and the endonuclease gene.

FIG. 4 lists the amino acid sequences of PshAI (SEQ ID NO:6) and EcoRV (SEQ ID NO:7) control proteins.

DETAILED DESCRIPTION OF THE INVENTION

Figure 5:
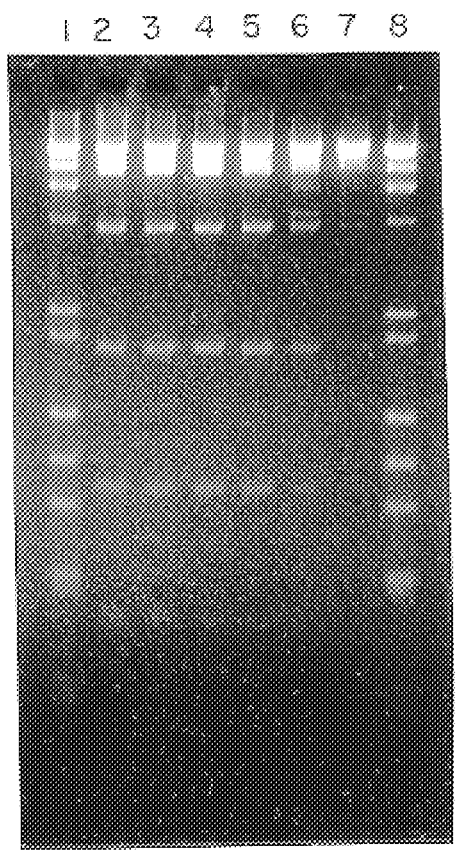
FIG. 5 is a photograph of an agarose gel demonstrating PshAI restriction endonuclease activity in cell extracts of *E. coli* ER2426 carrying the PshAI endonuclease on the pRRS derived plasmid pPshAIR1 and the PshAI methylase on the pSX34lazα derived plasmid pSX34PshAIM1. 1.5 gram of cell was suspended in 20 ml of sonication buffer (20 mM Tris-HCl, 1 mM dithiothreitol, 0.1 mM EDTA, pH 7.5) and broken by sonication, and clarified by centrifugation. The extract was used to digest 1 µg of λ DNA per 50 µl reaction volume in 1× NEBuffer 2, incubated at 30° C. for 30 minutes. Lanes 1 and 8: HindIII-λ+HaeIII-φX174 size standard; lane 2: 0.025 µl crude extract; lane 3: $1.25 \times 10^{-2}$ µl crude extract; lane 4: $6.25 \times 10^{-3}$ µl crude extract; lane 5: $3.13 \times 10^{-3}$ µl crude extract; lane 6: $1.56 \times 10^{-3}$ µl crude extract; lane 7: $7.81 \times 10^{-4}$ µl crude extract.

The present invention relates to recombinant DNA which encodes the PshAI restriction endonuclease and methylase, as well as to the enzymes produced from such a recombinant DNA.

The cloning of the PshAI restriction endonuclease gene from *Plesiomonas shigelloides* proved to be difficult. Methylase clones obtained by the methylase selection procedure failed to yield the endonuclease gene. The search for the endonuclease gene adjacent to the methylase gene was complicated by the presence of a 237 bp control gene between the methylase and endonuclease genes and an unidentified open reading frame 3' of the methylase gene that could have been a candidate for PshAI endonuclease. The PshAI endonuclease gene was finally identified by determining amino acid sequence at the amino-terminal end of the purified protein and comparing with the DNA sequence adjacent to the methylase gene.

The methylase selection method yielded two methylase clones. This procedure requires the methylase gene to express well enough in *E. coli* to methylate and thus protect the DNA from cleavage by the cognate endonuclease. A vector containing three PshAI sites was created by inserting a 10 bp oligomer containing a PshAI site into the SspI, SmaI and 1563 or 1582 DraI sites of pUC19 to form the vector pUC19PshAI. Vector libraries of *Plesiomonas shigelloides* DNA, partially cleaved by HinP1I, Sau3AI and NlaIII were constructed in the pUC19PshAI vector. Purified DNA of the three plasmid libraries was subjected to PshAI endonuclease digestion and transformed back into *E. coli*. Clones containing an active methylase gene are protected from PshAI digestion by virtue of methylase modification. This allows selection of clones carrying the methylase gene as such clones survive the endonuclease challenge intact. DNA from the survival clones was subsequently purified and the presence of an active methylase gene was judged by digesting with PshAI endonuclease. Two clones from the HinP1I library, pPshAIM19 and pPshAIM26, containing a 3 kb and 4.5 kb insert respectively, were protected from PshAI digestion. In order to determine the location and orientation of the methylase gene, pPshAIM19 was subjected to DNA sequencing. Amino acid translation of the DNA sequence yielded two motifs consistent with an $m_6 A\gamma$-type methylase (Wilson, *Methods in Enzymology*, 216:259–279 (1992), the disclosure of which is hereby incorporated by reference herein).

The methylase clones obtained from methylase selection were tested for endonuclease activity. No detectable endonuclease activity was observed. Either the PshAI endonuclease gene was present on the methylase clones but failed to express in *E. coli* at a detectable level or the methylase clones did not contain the PshAI endonuclease gene. From examining the DNA sequence of pPshAIM19 (FIG. 2), an open reading frame of 697 bp, referred to as ORF1 was observed 3' prime to the PshAI methylase gene. A synthetic DNA primer containing a restriction site at the ATG start codon of ORF1, along with another primer complementary to DNA sequences 3' to ORF1 was used to amplify the DNA of this gene. The amplified product was cloned into an expression vector, pAII17, but no detectable endonuclease activity was observed.

In order to locate and positively identify the PshAI endonuclease gene, the endonuclease protein was purified to near homogeneity and used to determine amino acid sequence at the amino-terminal end of the protein. The amino acid sequence obtained was compared with the DNA sequence adjacent to the methylase gene. The N-terminal amino acid sequence of the ORF1 did not match with the PshAI protein sequencing data, nor was any match to the PshAI protein sequence data found in the DNA sequence of clone pPshAIM19.

Since for most restriction-modification systems, the endonuclease is linked closely to the methylase, it was hypothesized that the PshAI endonuclease gene could be located 5' of methylase gene. To this end, the inverse PCR technique was used to characterize adjacent DNA 5' of methylase gene from *Plesiomonas shigelloides* genomic DNA. *Plesiomonas shigelloides* DNA was digested with various restriction endonucleases and a Southern hybridization using a 441 bp Sau3AI fragment (FIG. 2) as a probe was performed to identify fragments of suitable size for inverse PCR. Digestion of *Plesiomonas shigelloides* DNA with AvrII yielded a 2.9 kb fragment hybridized with the probe. Since an AvrII site is located 771 bp from the end of clone pPshAIM19 (FIG. 2), this fragment therefore contains approximately 2.1 kb of adjacent DNA 5' of the methylase clone. This DNA was amplified from *Plesiomonas shigelloides* genomic DNA by inverse PCR. (Ochman, et al., *Genetics*, 120:621 (1988), Triglia, et al., *Nucl. Acids Res.*, 16:8186 (1988) and Silver and Keerikatte, *J. Cell. Biochem.*, (Suppl.) 13E:306, Abstract No. WH239 (1989), the disclosures of which are hereby incorporated by reference herein).

Multiple attempts to clone this entire 2.9 kb inverse PCR product were unsuccessful. Because this DNA might contain an entire endonuclease gene, and therefore potentially be toxic to the host, DNA was fragmented for cloning into the vector pUC19. The 2.9 kb fragment was mapped by digesting with various endonucleases. A DraI site and an EcoRI site were found to be approximately 400 bp and 1400 bp away from the 5' end of the methylase clone (FIG. 3, the 3022 HinP1I site is the 5' end of the methylase clone pPshAIM19). The 1 kb EcoRI to DraI fragment was cloned into vector pUC19 and sequenced. To clone the 400 bp fragment between the 5' end of pPshAIM19 and the DraI site, oligonucleotide primers complementary to regions of known DNA sequences flanking this fragment were used to amplify this DNA by PCR, and the amplified product was cloned into pUC19 and sequenced.

The amino acid sequence obtained from protein sequencing of PshAI endonuclease was compared with the six frame amino acid translation of the DNA sequence 5' to the methylase gene. An open reading frame of 888 bp, ORF2 was identified in which the first 28 amino acid residues matched the amino-terminal sequence of the PshAI endonuclease. The PshAI endonuclease (ORF2) was separated from the PshAI methylase by an intervening open reading frame of 237 bp (ORF3) with significant homology to the EcoRV control (C) gene (FIG. 4). ORF3 is believed to be a PshAI control gene.

A two-step cloning strategy was attempted. In order to stabilize bacterial hosts containing the PshAI endonuclease gene, the DNA of the hosts was first methylated at PshAI sites by introducing the PshAI methylase gene on a separate vector which was compatible with the expression vector carrying the endonuclease gene. To this end, a PstI to XbaI fragment of pPshAIM19 (FIG. 1, the PstI site is located on the polylinker region of the pUC19PshAI vector) containing the entire methylase gene was cloned into the vector pSX34lacza (New England Biolabs, Inc.; Beverly, Mass.) which has a pSC101 type origin of replication. Clones expressing PshAI methylase were selected by the methylase selection method.

To clone the endonuclease without the control gene, a synthetic DNA primer was synthesized which included a PstI cloning site, stop codon in frame with the lacZ gene, an E. coli consensus strong ribosome binding site separated by seven bases from the ATG start codon of the PshAI endonuclease, a change of codon in amino acid number 2 to an E. coli preferred codon and 19 nucleotides matching the PshAI endonuclease DNA sequence for hybridization. The 3' (reverse) primer was designed to hybridize approximately 200 bp beyond the 3' end of the endonuclease gene. BamHI and EcoRI sites were introduced in the reverse primer to facilitate cloning. The endonuclease gene was amplified from genomic Plesiomonas shigelloides DNA. The amplified DNA was cleaved by PstI and BamHI and ligated into the expression vector pRRS, which had been previously cleaved by the same enzymes and gel purified. The ligation reaction was transformed into E. coli ER2426 competent cells carrying the PshAI methylase gene in pSX34lacza. Vectors containing inserts of the desired size were identified by miniprep procedures. These clones were grown to mid-log phase and induced with IPTG. The cells were then harvested by centrifugation, resuspended in sonication buffer and lysed by sonication. The extracts were assayed for PshAI endonuclease activity. One PshAI expressing host, pPshAIR1 was propagated and used to produce PshAI restriction endonuclease. The PshAI endonuclease was purified by a protein purification scheme described herein below.

The method described herein by which the PshAI restriction endonuclease and methylase genes are preferably cloned and expressed is illustrated in FIG. 1 and includes the following steps:

1. Plesiomonas shigelloides is grown in flasks containing L-Broth media, the cells are lysed and the genomic DNA purified.

2. The PshAI restriction endonuclease is partially purified from Plesiomonas shigelloides cells by a combination of protein purification techniques developed at New England Biolabs, Inc. (Beverly, Mass.) (see Example 1, step 2).

3. Random libraries of Plesiomonas shigelloides DNA are constructed. A vector containing three PshAI sites, pUC19PshAI, is formed by introducing a DNA oligomer containing a PshAI site into the SmaI, SspI and DraI (1563 or 1582) sites of pUC19. Plesiomonas shigelloides DNA is partially digested with HinP1I, Sau3AI and NlaIII respectively to produce fragments of an average size ranging from 2 kb–10 kb. These fragments are ligated with the vector pUC19PshAI. The ligated DNA is transformed into E. coli, the transformants are pooled and the populations of plasmids are purified to form libraries.

4. The methylation selection method is used to select for PshAI methylase clones. Each of the HinP1I, Sau3AI and NlaIII libraries are digested with PshAI endonuclease. The PshAI restricted plasmids are transformed back into E. coli to recover undigested clones. A number of individual transformants of plasmids surviving PshAI digestion are grown and mini-preparations are made of their plasmids. The plasmids are analyzed for resistance to PshAI endonuclease digestion. Two clones which are protected from PshAI cleavage and contain similarly sized HinP1I fragments are found. These clones, pPshAIM19 and pPshAIM26 from the HinP1I library contain inserts 3 kb and 4.5 kb respectively. The methylase positive clones are assayed for PshAI restriction endonuclease activity, but no activity can be detected.

5. Sequencing the PshAI methylase clones: The DNA of the 3 kb insert of clone pPshAIM19 is sequenced. An open reading frame containing amino acid sequences homologous to the conserved regions of an $m_6A\gamma$-type methylase is observed and identified as the PshAI methylase. A 697 bp open reading frame, ORF1, is observed 3' to the methylase gene separated from the methylase gene by 48 nucleotides. From restriction mapping it is observed that clone pPshAIM26 shares a common end 5' to the methylase gene as pPshAIM19, with the extra 1.5 kb of cloned DNA at the end of the clone 3' to the methylase gene. The ORF1 is cloned into an expression vector, grown, induced and assayed, but no PshAI activity is observed. An small open-ended ORF extending off the clone 5' to the methylase is observed.

6. The PshAI restriction endonuclease protein is purified to near homogeneity from Plesiomonas shigelloides by a combination of protein purification techniques developed at New England Biolabs (see Example 1, step 6). The endonuclease so purified is nearly homogeneous on SDS polyacrylamide gel electrophoresis and has an apparent molecular weight of approximately 35 kilodaltons.

7. The amino terminal amino acid sequence of the endonuclease is obtained using an Applied BioSystems Division, Perkin-Elmer Corporation (Foster City, Calif.) 470A Protein Sequencer (Brooks, et al., Nucleic Acids Research, 17:979–997 (1989), the disclosure of which is hereby incorporated by reference herein), and used to identify PshAI endonuclease gene in subsequent studies. The amino acid sequence of PshAI did not match with amino acid sequence deduced from the DNA sequence adjacent to the methylase gene on the methylase clones pPshAIM19.

8. Plesiomonas shigelloides DNA is digested with various restriction endonucleases. The digests are electrophoresed on an agarose gel and then transferred to immobilon-S transfer membrane (Millipore Corporation; Bedford, Mass.). Fragments containing DNA extending 5' to the methylase gene a30 hybridization, n hybridization, using a portion of pPshAIM19 as probe. A 2.9 kb AvrII fragment which should contain 2.1 kb of sequence 5' to pPshAIM19 is identified.

9. Plesiomonas shigelloides DNA is digested by AvrII endonuclease and the resulting fragments are ligated at low DNA concentration to favor intramolecular ligation. The circularized 2.9 kb fragment containing DNA corresponding to pPshAIM19 is amplified using two synthetic primers which anneal to the known sequence region and are oriented with their 3' ends toward the unknown region.

10. The amplified DNA 5' to the methylase is fragmented to disrupt the endonuclease, if present, cloned and sequenced. From mapping the 2.9 kb amplified product, a DraI and an EcoRI site are found to be located 400 bp and 1400 bp away from the 5' end of pPshAIM19. This 1 kb DraI to EcoRI fragment is subcloned into the vector pUC19 and the DNA is sequenced. The DNA between the 5' end of pPshAIM19 and the DraI site immediately upstream is amplified from *Plesiomonas shigelloides* DNA using synthetic primers flanking this region. The amplified product is cloned into the vector pUC19 and the DNA is sequenced.

11. The PshAI endonuclease gene is identified by comparing the amino acid translation of DNA sequence 5' to the methylase with the amino acid sequence data obtained from N-terminal amino acid sequencing of PshAI endonuclease. The start of the PshAI endonuclease gene is located 391 bp 5' from the start of the methylase gene, oriented in the opposite direction. An intervening open reading frame (ORF3) of 237 bp between the PshAI methylase and endonuclease genes is highly homologous to the EcoRV control gene, and is thus identified as the PshAI control gene.

12. Overexpressing the PshAI endonuclease gene:

A. General considerations

There are a number of ways in which the restriction gene can be overexpressed. The DNA sequence and detailed mapping information help determine the best approach for overexpression of the restriction endonuclease gene.

One approach for overexpression comprises designing primers that hybridize directly at the N-terminus of the restriction endonuclease gene and somewhere downstream (3') of the gene in order to use the polymerase-chain reaction to amplify the entire endonuclease gene. The resulting DNA fragment can be inserted into an expression vector such as pAII17 directly downstream of an inducible promoter (T7).

Alternatively, overexpression can be accomplished by inserting a promoter recognized strongly by *E. coli*, such as Ptac on pAGR3 (New England Biolabs, Inc.; Beverly, Mass.) directly in front of the beginning of the restriction endonuclease gene. This may be accomplished by finding convenient restriction sites near the beginning and end of the restriction endonuclease gene and compatible restriction sites near the promoter of pAGR3, and transferring the restriction gene into pAGR3 in line with the Ptac promoter. Other regulated promoters which can be used are PlacUV5 (Fuller, *Gene* 19:43–54 (1982), the disclosure of which is hereby incorporated by reference herein), and IPL (Shimatake and Rosenberg, *Nature* 292:128 (1981), the disclosure of which is hereby incorporated by reference herein) on pUC19 and pBR322 derivatives. In addition, a strong ribosome binding site (Shine & Dalgarno, *Proc. Natl. Acad. Sci. USA* 71:1342–1346 (1974), the disclosure of which is hereby incorporated by reference herein) can be placed in front of the gene to increase expression.

To obtain a stable clone which overexpresses the restriction endonuclease, the host is generally pre-protected from restriction endonuclease digestion. In the present invention this is accomplished by cloning the PshAI methylase on a separate plasmid. The plasmid used must be compatible with the expression vector. The methylase also must be produced at a level which will protect the host's genome from digestion by the overexpressed restriction endonuclease gene.

The DNA sequence of the gene can be altered by site-directed mutagenesis or by resynthesizing the gene itself to use codons that are more efficiently utilized in *E. coli* (Ikemura, *J. Mol. Biol.* 151:389–409 (1981), the disclosure of which is hereby incorporated by reference herein).

B. Cloning the PshAI methylase in a compatible vector

The PshAI methylase clone, pPshAIM19 is digested with PstI and XbaI to generate a 1660 bp fragment containing the entire methylase gene. This fragment is cloned into vector pSX34Iacza (New England Biolabs, Inc.; Beverly, Mass.). A population of colonies is subjected to one round of methylase selection and clones expressing the PshAI methylase are identified by introducing the vector pUC19PshAI (which contains three PshAI sites) into *E. coli* cells containing pSX34lacza methylase constructs, performing minipreps and digesting with PshAI. All clones tested expressed methylase activity well enough to fully protect plasmid pUC19PshAI from digestion by PshAI. Competent cells are made from a single clone, designated pSX34PshAIM1, for subsequent PshAI endonuclease expression.

C. Expression of PshAI endonuclease

DNA primers are designed and synthesized to amplify the entire PshAI endonuclease gene. The forward primer has the following elements: a PstI cloning site, stop codon in frame with the lacZ gene, *E. coli* consensus strong ribosome binding site, 7 nucleotide spacer sequence between the ribosome binding site and the ATG start codon of the PshAI endonuclease, a change of codo a usage in amino acid number 2 to an *E. coli* preferred codon and 19 nucleotides matching the PshAI endonuclease DNA sequence for hybridization. The 3' primer is designed to hybridize *Plesiomonas shigelloides* DNA approximately 200 bp beyond the 3' end of the endonuclease gene. BamHI and EcoRI sites were introduced in the reverse primer to facilitate cloning. The endonuclease gene is amplified from the genomic DNA using these primers. The amplified DNA is cleaved by PstI and BamHI and ligated into the expression vector pRRS, which has been previously cleaved by the same enzymes and gel purified. The ligation reaction is transformed into *E. coli* ER2426 competent cells containing pSX34PshAIM1. Vectors containing inserts of the desired size are identified by miniprep procedures. Several of these clones are grown to mid-log phase and induced with 0.5 mM IPTG for 5 hours. The cells are then harvested by centrifugation, resuspended in sonication buffer and lysed by sonication and the extract is assayed for PshAI endonuclease activity. One such PshAI expressing host, designated pPshAIR1, is propagated and used to produce PshAI restriction endonuclease.

13. Production: The PshAI endonuclease may be produced from host cells carrying the overexpressed PshAI restriction endonuclease gene and PshAI methylase gene by propagation in a fermenter in a rich medium with the appropriate antibiotic selection and induction. The cells are thereafter harvested by centrifugation and disrupted by sonication to produce a crude cell extract containing PshAI restriction endonuclease activity.

14. Purification: The crude cell extract containing the PshAI endonuclease is purified by a combination of protein purification techniques, such as affinity-chromatography or ion-exchange chromatography.

Although the above-outlined steps represent the preferred mode for practicing the present invention, it will be apparent to those skilled in the art that the above described approach can vary in accordance with techniques known in the art.

The following Example is given to illustrate embodiments of the present invention as it is presently preferred to practice. It will be understood that this Example is illustrative, and that the invention is not to be considered as restricted thereto except as indicated in the appended claims.

EXAMPLE 1

Cloning of PshAI Modification Methylase and Restriction Endonuclease Genes

1. DNA purification: A single colony of *Plesiomonas shigelloides* from an agar plate was innoculated into 1 L LB broth, grown overnight with shaking at 37° C. and the cells were pelleted by centrifugation. 3 g of cell paste was resuspended by gentle shaking in 20 ml of 25% sucrose, 0.05 M Tris-HCl, 1 mM EDTA, pH 8.0. 5 ml of 0.5M EDTA, pH 8.0 and 6 ml of freshly prepared 10 mg/ml lysozyme in 0.25 M Tris-HCl pH 8.0 was added and the solution was incubated at 4° C. for 2 hours. 24 ml of Lysis mix (1% Triton-X100, 50 mM Tris, 62.5 mM EDTA, pH 8.0) was added followed by 5 ml of 10% SDS and the solution was incubated at 4° C. overnight. The solution was extracted with 50 ml of equilibrated phenol, the aqueous phase was recovered and extracted with 50 ml of chloroform two times. The aqueous solution was dialysed against four changes of 2 L of 10 mM Tris, 1 mM EDTA, pH 8.0 overnight. The dialysed solution was then digested with RNase (100 ug/ml) at 37° C. for 1 hour. The DNA was precipitated by the addition of ¹⁄₁₀th volume 5M NaCl and 0.55 volume of 2-propanol and spooled onto a glass rod. The DNA was air dried and then dissolved in 10 ml of 10 mM Tris, 1 mM EDTA, pH 8.0.

2. Purification of the PshAI restriction endonuclease from *Plesiomonas shigelloides*: A colony of *Plesiomonas shigelloides* from an agar plate was innoculated into 1 L L-broth and grown 16 hours at 37° C. with shaking. The cells were harvested by centrifugation. All of the following procedures were performed on ice or at 4° C. 1 gram of cell pellet was resuspended in 10 ml of buffer A (20 mM Tris-HCl, 1 mM Dithiothreitol (DTT), 0.1 mM EDTA, pH 7.5) containing 1 mg/ml lysozyme and incubated on ice for 1 hour. 40 μl of 25% Triton-X100 was added to a final concentration of 0.1%. The cell suspension was frozen at −70° C. then thawed on ice. The extract was centrifuged at 15,000 rpm for 15 minutes at 40° C. and the supernatant was passed through a 0.22 micron filter. The supernatant was then loaded onto a 1 ml HiTrap™ Heparin column (Pharmacia; Piscataway, N.J.) equilibrated with buffer A containing 50 mM NaC. The column was washed with 10 ml of buffer A containing 50 mM NaCl, followed by a 40 ml linear gradient from 0.05M NaCl to 1M NaCl in buffer A. 1.5 ml fractions were collected. Fraction were assayed for PshAI restriction activity using λ DNA. The peak of restriction enzyme activity eluted from the column between 0.3 and 0.4M NaCl. Two heparin column fractions were pooled, diluted with 5 volumes buffer A and applied to a 1 ml Hitrap™ Q column (Pharmacia; Piscataway, N.J.) equilibrated in buffer A containing 50 mM NaCl. The column was washed with 10 ml of buffer A containing 50 mM NaCl and then a 40 ml linear gradient of 0.05M NaCl to 0.6M NaCl in buffer A was applied and 1 ml fractions were collected. The PshAI restriction enzyme activity eluted between 0.2 and 0.25M NaCl. Fractions containing PshAI were mixed with an equal volume of glycerol and stored at −20° C. The HiTrap™ Q fractions were assayed on λ DNA and found to contain approximately 6000 units of PshAI.

3. Construction of random libraries of *Plesiomonas shigelloides* DNA in a selectable vector.

A. Construction of a selectable vector

A DNA oligomer was synthesized containing a PshAI site (along with an EagI site) as follows. The 5' G residue was phosphorylated to facilitate ligation.

PshA I linker: 5'-pGACGGCCGTC-3' (SEQ ID NO:8) Three sites on vector pUC19 were chosen into which to introduce the linker; SmaI (412), SspI (2501) and DraI at either (1563 or 1582), but not at DraI (2274). Linker was first inserted into each of these three sites separately, then the pUC19PshAI vector containing three PshAI sites was created by ligating together appropriate fragments of the single insertion vectors to form the intact pUC19PshAI vector.

(1): Constructing vector with 1 PshAI site, pDraI, pSmaI and pSspI: PshAI linker at 1 μM concentration was heated at 65° C. for 2 mins and allowed to self-anneal by slowly cooling to room temperature. pUC19 was linearized by digestion with SmaI, and SspI and DraI respectively. Since pUC19 has three DraI sites, pUC19 was partially digested with DraI and the 2686 bp fragment corresponding to cleavage at a single DraI site was gel purified. The cleaved pUC19 DNAs was dephophorylated with Calf Intestinal Alkaline Phosphatase (CIP) according to the manufacturer's instruction. 1 μl of 1 μM annealed linker was ligated with each digested and dephophorylated vector pUC19 (50 ng) in a 20 μl reaction volume using 400 U (New England Biolabs, Inc.; Beverly, Mass.) of T4 DNA ligase for 2 hours at 16° C. The ligation mixture was transformed into *E. coli* strain ER 2420 and plated on L-broth plates containing 100 μg/ml ampicillin for individual colonies. Clones of the desired construct were identified by performing minipreps, digesting the purified DNA with PshAI and analyzing it by agarose gel electrophoresis.

Analysis of plasmid clones: Individual transformants were inoculated into 1.8 ml cultures of L-broth containing ampicillin and the plasmids that they carried were prepared by the following miniprep plasmid purification procedure, adapted from the method of Birnboin and Doly (*Nucleic Acids Res.* 7:1513 (1973), the disclosure of which is hereby incorporated by reference herein) as described below. Plamids were assayed for the presence of linker by digesting with PshAI.

Miniprep Procedure: 1.5 ml of each culture was centrifuged at 8000 rpm for 2 minutes; the supernatant was discarded and the cell pellet was resuspended in 200 μl of 25 mM Tris, 10 mM EDTA, 50 mM glucose, pH 8.0. 400 μl of a freshly prepared solution of 0.2M NaOH, 1% SDS was added to each tube and the tubes were shaken to lyse the cells. Once the solutions had cleared, 300 μl of 3M NaAcetate pH 4.8 was added to each and gently mixed by shaking. The precipitates that formed were spun down at 14,000 rpm at 4° C. for 3 minutes. Each supernatant was poured into a centrifuge tube containing 700 μl of isopropanol and mixed. The tubes were spun at 14,000 rpm at 4° C. for 5 minutes to pellet the precipitated nucleic acids. The supernatants were discarded and the pellets were air-dried at room temperature for 15 minutes. Once dried, the pellets were dissolved in 250 μl of 10 mM Tris pH 8.0, 1 mM EDTA, containing 50 μg/ml RNase and incubated for 1 hour at 37° C. to digest the RNA. The DNA was precipitated by the addition of 25 μl of 5M NaCl followed by 175 μl of 2-propanol. The DNA was collected by centrifugation for 5 minutes at 4° C., the supernatants were discarded, the pellets were dried and then redissolved in 50 μl of 10 mM Tris, 1 mM EDTA pH 8.0 (1× TE). The plasmid minipreps were subsequently analyzed by digestion with various restriction enzymes.

To remove oligomerized multiple linker inserts, the miniprep DNA of the desired clones was digested with EagI and gel purified. 20 ng of the digested DNA was used to self-ligate in a 20 μl reaction volume using 400 U T4 DNA ligase at 16° C. overnight. The ligation mixture was transformed into *E. coli* ER2420 and plated on L-broth plates containing ampicillin (100 μg/ml). Plamids were isolated from individual colonies, using the miniprep procedure as described. Clones of the desired construct were identified by digesting the plasmid with PshAI and analyzing by agarose gel electrophoresis. Plasmid from a clone of each construct, designated pSmaI, pDraI and pSspI respectively, was used in the subsequent steps.

(2): Constructing vectors with 2 PshAI linker sites, pSmaISspI and pDraISmaI: Three unique sites, EcoO109I, BsrFI, and AflIII on vector pUC19 were chosen to generate fragments containing the PshAI linker insertions. 1 μg of the vector pSmaI and pSspI each were cleaved with EcoO109I and BsrFI to give 895 bp and 1791 bp fragments respectively. The 1791 bp fragment of pSmaI and the 895 bp fragment of pSspI were gel purified. Approximately 20 ng of each fragment were ligated in a 20 μl reaction using 400 U of T4 DNA ligase at 16° C. for 2 hours. The ligation reaction was transformed into E. coli ER2420 and plasmids were isolated from individual colonies. Clones of the desired construct was identified by PshAI digestion. One such construct, pSmaISspI was used in the subsequent steps.

Similarly, 1 μg of the vector pSmaI and pDraI each was cleaved by BsrFI and AflIII to give 973 bp and 1713 bp fragments respectively. The 1713 bp fragment of pSmaI and 973 bp fragment of pDraI were gel purified. Approximately 20 ng of each fragment was ligated together in a 20 μl reaction using 400 U of T4 DNA ligase at 16° C. for 2 hours. The ligation reaction was transformed into E. coli ER2420 and the desired constructs were identified as described above. One such construct, pSmaIDraI was used in the subsequent steps.

(3): Constructing vector with 3 PshAI sites, pUC19PshAI: 1 μg of vectors pSmaISspI and pDraISmaI was digested with EcoO109I and BsrFI to give 895 bp and 1791 bp fragments. The 1791 bp fragment of pDraISmaI and the 895 bp fragment of pSmaISspI were gel purified. 20 ng of each gel purified fragment was ligated in a 20 μl reaction using 400 U of T4 DNA ligase at 16° C. for 2 hours. The ligation reaction was transformed into E. coli ER2420 and the desired constructs were identified as described above. One such construct containing three PshAI sites, pUC19PshAI, was used for PshAI genomic libraries construction.

B: Constructing PshAI genomic libraries

10 μg of Plesiomonas shigelloides genomic DNA was partially digested with NlaIII, Sau3AI, HinP1I respectively by serially diluting the restriction endonucleases from 1 unit per μg of Plesiomonas shigelloides genomic DNA to ⅟₆₄th unit per μg by a factor of two each dilution. Fragments between 2 kb and 10 kb were gel purified from a low melting point agarose gel. 1.5 μg of the gel purified NlaIII, Sau3AI, HinP1I partially digested DNA was ligated to 0.5 μg vector Puc19PshAI which had been previously cleaved by SphI, BamHI and AccI respectively and dephosphorylated with calf intestinal alkaline phosphatase in 200 μl of 1× T4 DNA ligase buffer containing 1000 units of T4 DNA ligase (New England Biolabs, Inc.; Beverly, Mass.) for 16 hours at 17° C. 30 μl the of ligation reactions was transformed into ER2426 and plated on L-broth plates containing 100 μg/ml ampicillin. 24,000, 21,000, and 19,000 individual transformants were obtained from transforming the HinP1I, Sau3AI, and NlaIII ligation reactions respectively. The colonies from each library were scraped into 6 ml of 10 mM Tris, 10 mM $MgCl_2$, pH 7.5, mixed well, then 600 μl of each pool was inoculated into 50 ml of L-broth containing 200 μg/ml ampicillin and allowed to grow at 37° C. with shaking. Plasmids were isolated using a 25× scale-up of the miniprep procedure as described above. The miniprep DNA was resuspended in 400 μl of 1×TE and centrifuged at 14,000 rpm for 5 minutes. 352 μl of the cleared supernatant was transfered into a fresh tube and mixed with 88 μl of 4M NaCl and 440 μl of 13% PEG 8000 and incubated on ice for 15 minutes. The tube was spun at 14,000 rpm at 4° C. for 5 minutes to pellet the precipitated supercoiled plasmid DNA. The supernatant was discarded and the DNA pellet was washed with ice cold 70% ethanol. The DNA was pelleted again by centrifuging at 14,000 rpm for 5 minutues at 4° C. The supernatant was discarded and the pellet was dried then dissolved into 250 μl of 1× TE to form the primary plasmid library.

4. PshAI methylase selection: 1 μg of DNA from each library was digested in 50 μl 1× NEBuffer 2 with 8 U, 4 U, 2 U and 1 U of the PshAI endonuclease prepared in step 2 above respectively at 30° C. for 2 hours. 50 ng (2.5 μl) of the PshAI digested DNA was transformed into E. coli ER2416 and plated on L-broth plates containing 100 μg/ml ampicillin. A total of 108 transformants from the 3 libraries were analyzed as follows: Plasmid from each colony was isolated by miniprep procedure and digested with PshAI endonuclease. Four clones, pPshAIM19, pPshAIM20, pPshAIM26 and pPshAIM33, all from the HinP1I library, were found to be fully protected from PshAI digestion. Further restriction analysis showed that pPshAIM19 and pPshAIM20 were identical, containing a 3 kb insert, and that pPshAIM26 and pPshAIM33 were identical and contained a 4.5 kb insert. pPshAIM26 contained the same 3 kb of Plesiomonas shigelloides as pPshAIM19 plus an additional 1.5 kb of DNA located 3' to the methylase gene.

5. DNA Sequencing: DNA sequencing of the 3 kb insert on pPshAIM19 was performed using the Circumvent™ DNA sequencing kit (New England Biolabs, Inc.; Beverly, Mass.) according to the manufacturers instructions. Various HinP1I and Sau3AI subclones of pPshAIM19 were made in vector pUC19 and synthetic oligonucleotide primers were synthesized to accomplish the sequencing. Miniprep DNA preparations of pPshAIM19 were used as templates. The six frame amino acid sequence translated from the DNA sequence was compared with the homologous region of various methylases and motifs I and IV of $m_6A\gamma$-type methylase were identified. The DNA sequence of motif I was found to be 5'-GGACAGTTTTTCACTCCA-3' (SEQ ID NO:9) and 5'-TTAGATCCAGCATGCGGCTCAGGAGGCTTTCTT-3' (SEQ ID NO:10), which translates into the amino acid sequence: GQFFTP (SEQ ID NO:11) and LDPACGSGGFL (SEQ ID NO:12), where the amino acids in bold match the conserved or nearly conserved residues. The DNA sequence of motif IV was found to be 5'-GATGCGATACTCACAAACCCTCCGTTT-3' (SEQ ID NO:13) which translates into the amino acid sequence: DAILTNPPF (SEQ ID NO:14). A putative start site ATG was identified 8 nucleotides away from a promising ribosome binding sequence: 5'-GGAGAG-3' (SEQ ID NO:15). A putative stop site was also identified. The methylase gene so identified is 1176 bp long.

A 697 bp open reading frame, designated ORF1, was observed 3' to the methylase gene, oriented in the same direction as the methylase gene and separated from it by 48 nucleotides. This ORF1 was cloned into the expression vector pAII17 to express the gene to test if it was the PshAI endonuclease. Two DNA oligomer primers were synthesized to amplify ORF1 from Plesiomonas shigelloides DNA such that it could be placed into the NdeI site of the expression vector pAII17. Although multiple clones of this gene were examined, no PshAI activity was observed. An open-ended ORF of 50 bp extending off the pPshAIM19 clone 5' to the methylase and oriented in the opposite direction was observed. Since the open reading frame 3' to the methylase, ORF1, did not seem to be the PshAI endonuclease gene, it was thought that this beginning of an open reading frame 5' to the methylase might be the endonuclease. To unambiguously identify the PshAI endonuclease gene amino acid sequence data of the PshAI endonuclease was needed. To this end, PshAI endonuclease was purified to near homogeneity and the its N-terminal amino acid sequence was determined.

6. Purification of the PshAI restriction endonuclease from *Plesiomonas shigelloides* to near homogeneity. A colony of *Plesiomonas shigelloides* from an agar plate was innoculated into 6 L L-broth and grown overnight at 37° C. with shaking. The cells were harvested by centrifugation. All of the following procedures were performed on ice or at 4° C. The cell pellet (15 g) was resuspended in 50 ml of buffer A (20 mM Tris-HCl, 1 mM Dithiothreitol (DTT), 0.1 mM EDTA, pH 7.5) containing 1 mg/ml lysozyme and incubated on ice for 1 hour. 200 µl of 25% Triton-X100 was added to a final concentration of 0.1%. The cell suspension was frozen at −70° C., then thawed on ice. The extract was centrifuged at 15,000 rpm for 15 minutes at 4° C. and the supernatant was loaded onto a 25 ml heparin-sepharose column equilibrated in buffer A containing 100 mM NaCl. The column was washed with 60 ml of buffer A containing 100 mM NaCl, followed by a 250 ml linear gradient from 0.1M NaCl to 0.6M NaCl in buffer A. 5 ml fractions were collected. Fractions were assayed for PshAI restriction activity with λ DNA and the peak of restriction enzyme activity eluted from the column between 0.32 and 0.4M NaCl and was pooled. The amount of protein was estimated to be 10 mg and contained approximately 480,000 units of PshAI activity. This heparin-sepharose pool was diluted with 2 volumes of buffer A and applied to a 3 ml heparin-TSK FPLC column (TosoHaas; Philadelphia, Pa.) equilibrated in buffer A containing 100 mM NaCl. The column was washed with 10 ml of buffer A containing 100 mM NaCl followed by a 40 ml linear gradient of 0.1M NaCl to 0.6M NaCl in buffer A. 1 ml fractions were collected. Fractions were assayed for PshAI activity with λ DNA. The peak of restriction enzyme activity eluted between 0.32 and 0.35M NaCl and 3 fractions were pooled. This heparin-TSK pool contained approximately 390,000 units PshAI activity and was diluted with 2 volumes of buffer A and loaded onto a 1 ml Mono Q FPLC column (Pharmacia; Piscataway, N.J.) equilibrated with buffer A containing 100 mM NaCl. The column was washed with 5 ml of buffer A containing 100 mM NaCl followed by a 40 ml linear gradent from 0.1M NaCl to 0.6M NaCl in buffer A. The peak of restriction enzyme activity eluted at 0.25M NaCl and contained approximately 250,000 units of PshAI activity. 8 µl of the peak fraction was loaded on an SDS-PAGE protein gel and subjected to electrophoresis. The gel was stained with Coomassie blue R-250 and only one prominant band at approximately 35 kD was observed.

7. Amino terminal PshAI protein sequence: The approximately 35 kD protein band obtained was subjected to amino terminal protein sequencing on an Applied BioSystems Division, Perkin-Elmer Corporation (Foster City, Calif.) Model 407A gas phase protein sequencer (Brooks, et al., *Nucleic Acids Research*, 17:979–997 (1989), the disclosure of which is hereby incorporated by reference herein). The sequence of the first 28 residues obtained was the following: MSILDNEKQLXILNIINEGVTPAIIPEL (SEQ ID NO:16). This amino acid sequence data from the amino terminus of the PshA I endonuclease protein did not match the deduced amino acid sequence of ORF1 or the small open ended or (ORF3) extending off the methylase clones 5' to the methylase. It was subsequently used to compare with amino acid sequence deduced from the DNA sequence 5' to the methylase gene, obtained as described below, to identify the endonuclease gene.

8. Southern hybridization:

A. Preparation of the filter 1.5 µg of *Plesiomonas shigelloides* genomic DNA was digested with restriction endonucleases AflIII, AvrII, FspI and MslI respectively. The digests were electrophoresed on a 0.8 % agarose gel. The gel was washed in two changes of 250 ml of 0.25M HCl for 15 minutes each, then in two changes of 250 ml of 0.5M NaOH, 1.5M NaCl for 15 minutes each and finally in two changes of 250 ml of 1M NH$_4$OAC, 0.02 M NaOH for 30 minutes each at room temperature. To transfer the DNA to immobulin S membrane, the membrane was cut 1 cm larger then the gel on all sides (10 cm×8 cm) and was placed on the bottom side of the gel. This was placed on top of a two inch high stack of paper towels. A glass plate was placed on the top of the stack and a small weight was placed on the plate. The DNA transfer was allowed to proceed overnight. The immobulin S membrane was thoroughly dried then the DNA was UV cross-linked to the membrane by exposure to 33.33 joules/cm$^2$ UV light for 30 minutes in a UV crosslinker, X Linker-254 (Automated BioSystems, Inc.; Essex, Mass. and Owl Scientific, Inc.; Woburn, Mass.).

B. Biotinylation of the probe

Approximately 10 µg of pPshAIM19 was digested with 20 U of Sau3AI for 1 hour at 37° C. in 100 µl reaction volume. A 441 bp Sau3AI fragment from the end of the clone 5' to the methylase gene (bp 2354 to 2795, FIG. 2) was gel purified and resuspended in 37 µl of nuclease free dH$_2$O (New England Biolabs, Inc.; Beverly, Mass.). This DNA was denatured at 95° C. for 5 minutes and then biotinylated according to the manufacturer's instructions (NEBlot™ Phototope™ Kit; New England Biolabs, Inc.; Beverly, Mass.).

C. Hybridization

The blot from section A was wet with 6× SSC at room temperature for 2 minutes then prehybridized at 68° C. in 8 ml of prehybridization solution composed of 5× Denhardt's solution, 6× SSC, 0.5% SDS, and 100 µg/ml denatured herring sperm DNA for 1 hour. The biotinylated probe was denatured at 95° C. for 5 minutes then mixed with 8 ml prehybridization solution to a final concentration of 20 ng/ml and the blot was transferred to this solution. The hybridization was carried out at 55° C. overnight. The blot was then washed with two changes of 250 ml 2× SSC, 0.1% SDS for 5 minutes each at room temperature followed by two changes of 250 ml 0.2× SSC, 0.1% SDS for 15 minutes each at 55° C.

D. Phototope® detection

All solutions used were made with MilliQ™ dH$_2$O. The blot was gently shaken in 8 ml of Blocking solution (5% SDS, 17 mM Na$_2$HPO$_4$, 8 mM NaH$_2$PO$_4$, pH 7.2) for 5 minutes, then in 8 ml of Blocking solution containing 1 µg/ml streptavidin for 5 minutes. The blot was washed with two changes of 40 ml wash solution I (diluted 10× from blocking solution) for 5 minutes each. It was next treated with 0.5 µg/ml of biotinylated alkaline phosphatase in 8 ml of blocking solution for 5 minutes and washed with two changes of 40 ml wash solution II (10 mM Tris, 10 mM NaCl, 1 mM MgCl$_2$, pH 9.5) for 5 minutes each. The DNA was detected by treating the blot with 2 ml of Lumigen-PPD reagent in Lumigen diluent (New England Biolabs, Inc.; Beverly, Mass.) for 5 minutes and exposed to X-ray film for 30 minutes at room temperature. From this blot, a 2.9 kb AvrII fragment containing approximately 800 base pairs of DNA coincident with the pPshAIM19 clone and 2100 base pairs of DNA extending 5' to this clone was identified.

9. Inverse PCR amplification: 6 µg of *Plesiomonas shigelloides* DNA was digested by 30 units AvrII restriction endonuclease in 100 µl reaction volume for 1 hour at 37° C. The enzyme was removed by extracting once with an equal volume of equilibrated phenol:CHCl$_3$ (50:50, v/v) and once with CHCl$_3$. The DNA was precipitated by adding 1/10th volume of 5M NaCl and 1 volume of 2-propanol, pelleted by centrifugation, washed with ice cold 70% ethanol and dried. It was then resuspended in 50 μl of 1× TE.

One μg of the AvrII digested DNA was circularized at a concentration of 1 μg/ml in 1× ligase buffer using 4000 U of T4 DNA ligase at 16° C. overnight. Enzyme was removed by extracting once with equlibrated phenol:CHCl$_3$ (50:50, v/v) and once with CHCl$_3$. The DNA was precipitated by adding 1/10th volume of 5M NaCl and 1 volume of 2-propanol, pelleted by centrifugation, washed with ice cold 70% ethanol and dried. It was then resuspended in 50 μl of 1× TE buffer and used as the template in the following inverse PCR reaction.

Primer PshAI-17 and PshAI-18 of sequences shown below were synthesized.

Primer PshAI-17
5'-GAGGGGTAGTTTCTGAGTGMGACC-3' (SEQ ID NO:17)

Primer PshAI-18
5'-AATACGTTATCACTATAAATATCC-3' (SEQ ID NO:18)

In the reaction that was successful in amplifying the product, a reaction mix was made by combining:

10 μl of 10× Vent™ reaction buffer
6 μl of 4 mM dNTP solution
5 μl of primer PshAI-17 at 10 uM concentration
5 μl of primer PshAI-18 at 10 uM concentration
4 μl of 100 mM MgSO$_4$ (6 mM Mg$^{++}$ final concentration)
10 μl of DNA template (approximately 200 ng)
68 μl dH$_2$O
2 μl of Vent™ Exo$^-$ polymerase (NEB#257 (2 unit/ul)

The PCR amplification conditions were: 95° C. for 2 minutes for one cycle, followed by 25 cycles of 95° C. for 20 seconds, 56° C. for 30 seconds and 72° C. for 3 minutes. 10 μl of the PCR reaction was analyzed by electrophoresis on a 0.8% agarose gel. A prominent band of approximately 2.9 kb was observed, as was some primer dimer product. To obtain a greater quantity of this product, the 2.9 kb band was gel purified and used as the template in subsequent PCR reactions carried out as above. The 2.9 kb product obtained was gel purified and resuspended in 50 μl of 1× TE.

10. Cloning the DNA 5' to the methylase gene clones: The 2.9 kb inverse PCR product was first fragmented by restriction enzyme digestion and then cloned into pUC19.

A. Cloning the 1 kb EcoRI, DraI piece

The 2.9 kb PCR amplified product was mapped using various endonucleases to find convenient sites for cloning. A DraI site was found 400 bp from the 5' end of pPshAIM19 and an EcoRi site was located 1400 bp from the 5' end of pPshAIM19 (FIG. 3). 4 μg of the 2.9 kb amplified product was digested with EcoRI and DraI in 100 μl reaction volume at 37° C. for 1 hour. The reaction was extracted once with equlibrated phenol:CHCl$_3$ (50:50 v/v), and once with CHCl$_3$. DNA was precipitated with 1/10th volume of 5M NaCl and 1 volume of 2-propanol, pelleted by centrifugation and washed with ice cold 70% ethanol. The DNA was resuspended in 40 μl of 1× TE and 2 μl was ligated into pUC19 (50 ng previously digested with HincII and EcoRI and gel purified) using 400 U T4 DNA ligase in 20 μl volume at 16° C. for 2 hours. 10 μl of ligation mixture was transformed into ER 2426 and plated on L-broth plates containing 100 ug/ml ampicillin for individual colonies. The plasmids were isolated by performing minipreps. The desired construct was identified by restriction enzyme digestion. DNA sequencing was performed using the Circumvent™ DNA sequencing kit (New England Biolabs, Inc.; Beverly, Mass.) according to the manufacturer's instructions, using M13/pUC primers NEB#1224 and NEB#1233 as well as custom synthesized primers.

B. To obtain DNA sequence information for the 400 bp region between the DraI site and the 5' end of pPshAIM19, a PCR product was made using two primers, PshAI-39 and PshAI-42 which were synthesized to anneal at the flanking regions. *Plesiomonas shigelloides* genomic DNA was used as the template. A 1.5 kb product as expected was obtained. The PCR reaction condition was as follows:

10 μl of 10× Vent™ reaction buffer
6 μl of 4 mM dNTP solution
5 μl of primer PshAI-39 at 10 uM concentration
5 μl of primer PshAI-42 at 10 uM concentration
4 μl of 100 mM MgSO$_4$ (6 mM Mg$^{++}$ final concentration)
1 μl (100 ng) of *Plesiomonas shigelloides* genomic DNA
79 μl dH$_2$O
0.5 μl (1 unit) Vent™ DNA Polymerase (2 unit/ul)

The PCR amplification conditions were: 95° C. for 2 minutes for one cycle, followed by 20 cycles of 95° C. for 30 seconds, 56° C. for 30 seconds and 72° C. for 1.6 minutes.

DNA sequencing was performed using Circumvent™ DNA sequencing kit (New England Biolabs, Inc.; Beverly, Mass.) according to the manufacturers instructions. Various subclones of this 1.5 kb PCR product were made in vector pUC19 and sequenced using M13/pUC primers NEB# 1224 and NEB# 1233. Miniprep DNA of the sub clones was used as template.

11. PshAI Restriction-Modification system: Two open reading frames were found 5' to the methylase gene by examining the 6 frame amino acid translation of the DNA sequence (FIG. 3). An open reading frame, ORF3 of 237 bp was located 152 bp 5' to the methylase gene and running in the opposite orientation. The amino acid sequence of this open reading frame shows strong homology to other putative restriction control, or C, proteins (Tao, et al., *J. of Bacteriology*, 183:1367–1375 (1991), the disclosure of which is hereby incorporated by reference herein), and was most homologous to the EcoRV C protein. FIG. 4 shows an alignment of the PshAI C protein with EcoRV C protein. The second open reading frame, ORF2, was located 11 bp 3' to the C gene, was 888 bp in length and was oriented in the same direction as the C gene. This orf was identified as the PshAI endonuclease gene since the amino acid sequence deduced from the DNA sequence at the 5' end of this open reading frame matched exactly with the first 28 residues from N-terminus amino acid sequencing of the PshAI endonuclease gene. The ambiguous residue X at position 11 of the amino acid sequencing results was found to be an arginine.

12. Overexpressing the PshAI endonuclease:

A. Subcloning the PshAI methylase on a compatable vector pPshAIM19 DNA was digested with PstI and X baI and the resulting 1.6 kb fragment containing the entire methylase gene was gel purified. This 1.6 kb fragment was ligated to vector pSX34lacZα previously cleaved with the same enzymes and gel purified. The ligation reaction was transformed into ER2426 and approximately 300 colonies were obtained. The colonies were washed off the agar plate with 3 ml of 10 mM Tris, 10 mM MgCl$_2$, pH 7.5 and inoculated into 50 ml of L-broth containing 25 μg/ml chloramphenicol and grown at 37° C. overnight with shaking. The cells were pelleted by centrifugtion at 5,000 rpm for 5 minutes and the plasmid DNA was purified by a maxi-miniprep procedure (5× scale of the miniprep procedure described above). Approximately 1.5 µg of purified DNA was digested with 20 U of PshAI in 100 µl volume at 30° C. for 1 hour, then phenol/chloroform extracted and precipitated with ⅒th volume of 5M NaCl and 1 volume of 2-propanol. Approximately 600 ng of the PshAI digested DNA was transformed into ER2426 and plated on L-broth plates containing 25 µg/ml chloramphenicol for individual transformant. 10 single colonies were innoculated into 10 ml of L-broth containing 25 µg/ml chloramphenicol and plasmid DNA was purified by miniprep procedure. To test for PshAI methylase activity, the vector Pucl9PshAI, which has three PshAI sites, was cotransformed with the ten putative pSX34lacZα PshAI methylase clones into ER2426 and plated on L-broth plates containing 100 µg/ml ampicillin and 25 µg/ml chloramphenicol. Individual transformants were miniprepped and digested with PshAI. Plasmid DNA from all clones examined was fully protected against PshAI cleavage. The methylase containing plasmid of one such clone was designated as pSX34PshAIM1 and used for endonuclease expression.

B. Endonuclease cloning

The restriction endonuclease gene was expressed by inserting the gene into a expression vector, pRRS, directly downstream of a strong inducible promotor (PlacUV5) and strongly recognized ribosome binding site. To accomplish this, two oligonucleotide primers were made utilizing the DNA sequence data. The first oligonucleotide primer contained a PstI site to facilitate cloning, a stop codon in frame with the lacZ gene to terminate translation of the lacZ protein, a strong recognized ribosome binding site, seven nucleotide spacer between the rbs and the ATG start codon of the PshAI gene, a change in codon usage for serine at residue 2 to an E. coli preferred codon and sequence complementary to Plesiomonas shigelloides DNA for hybridization:

Primer PshAI-46
5'-GAGACTGCAGGAGGTMTTMTATGTC CATTTTAGATAATGAAAAAC-3' (SEQ ID NO:19)

The reverse primer was designed to hybridize approximately 200 bp 3' to the 3' end of the endonuclease gene and had BamHI and EcoRI sites added to facilitate cloning:

Primer PshAI-47
5'-GTAGMTTCGGATCCGGCGAATGAG AG-3' (SEQ ID NO:20)

These two primers were used to amplify the PshAI endonuclease gene from Plesiomonas shigelloides genomic DNA by combining:

10 µl 10× Vent™ reaction buffer
6 µl of 4 mM dNTPs
3 µl (900 ng) Plesiomonas Shigelloides genomic DNA
5 µl (10 uM stock) primer PshAI-46
5 µl (10 uM stock) primer PshAI-47
6 µl of 100 mM MgSO$_4$ (8 mM Mg$^{++}$ final concentration)
65 µl dH$_2$O
0.8 µl (1.6 units) Vent™ polymerase (2 unit/µl stock)

and amplifying at 95° C. for 2 minutes for 1 cycle, followed by 4 cycles of 95° C. for 30 seconds, 40° C. for 30 seconds, 72° C. for 1 minute, followed by 20 cycles of 95° C. for 30 seconds, 65° C. for 30 seconds and 72° C. for 1 minute. The amplification product of approximately 1.1 kb was gel purified, cleaved with PstI and BamHI, phenol-chloroform extracted, precipitated, resuspended in 1× TE and ligated into pRRS vector previously cleaved with PstI and BamHI and gel purified. The ligation reaction was transformed into E. coli strain ER 2426 previously modified with the PshAI methylase gene construct pSX34PshAIM1. Out of 14 individual transformants analyzed, 12 expressed PshAI endonuclease activity. One of these clones was selected for producing the PshAI endonuclease and given the strain designation of NEB #984. A titration of the PshAI restriction endonuclease activity produced from crude extracts of NEB #984 is shown in FIG. 5. The enzyme titer was approximately 10$^7$ u/g of cells.

13. The PshAI restriction endonuclease may be produced from NEB #984 by propagation to mid-log phase in a fermenter containing L-broth medium with ampicillin (100 µg/ml) and chloramphenicol (25 µg/ml). The culture is induced by the addition of IPTG to a final concentration of 0.3 mM and allowed to continue growing overnight (16 hours). The cells are harvested by centrifugation and may be stored at −20° C. or used immediately.

14. Purification of the PshAI restriction endonuclease from NEB#948 can be accomplished by a combination of standard protein purification techniques, such as affinity-chromatography or ion-exchange chromatography, as outlined in step 6 above. The PshAI restriction endonuclease obtained from this purification is substanially pure and free of non-specific endonuclease and exonuclease contamination.

A sample of the E. coli containing both pSX34PshAIM1 and pPshAIR1 (NEB#984) has been deposited under the terms and conditions of the Budapest Treaty with the American Type Culture Collection on Feb. 27, 1996 and received ATCC Accession Number 69999.

What is claimed is:

1. Isolated DNA coding for the PshAI restriction endonuclease, wherein the isolated DNA is obtainable from *Plesiomonas shigelloides*.

2. A recombinant DNA vector comprising a vector into which a DNA segment coding for the PshAI restriction endonuclease has been inserted.

3. Isolated DNA coding for the PshAI restriction endonuclease and methylase, wherein the isolated DNA is obtainable from ATCC No. 69999.

4. A cloning vector which comprises the isolated DNA of claim 3.

5. The cloning vector of claim 4, wherein the cloning vector comprises pPshAIR1.

6. A host cell transformed by the cloning vector of claim 2, 4, or 5.

7. A method of producing an PshAI restriction endonuclease comprising culturing a host cell transformed with the vector of claim 2, 4, or 5 under conditions suitable for expression of said endonuclease.

* * * * *

UNITED STATES PATENT AND TRADEMARK OFFICE
CERTIFICATE OF CORRECTION

PATENT NO. : 5,824,529  
DATED : October 20, 1998  
INVENTOR(S) : Chang, et al.

Page 1 of 3

It is certified that error appears in the above-identified patent and that said Letters Patent is hereby corrected as shown below:

Column 1, line 37, replace "GMTTC" with --GAATTC--

Column 3, line 6, replace "Fomenka" with --Fomenkov--

Column 4, line 61, replace "purifells" with --the cells--

Column 8, line 60, replace "a 30 hybridization" with --are Identified by Southern--

Column 10, line 5, replace "pSX34Iaczα" with --pSX34laczα--

Column 10, line 22, replace "codo a" with --codon--

Column 11, line 32, replace "at 40°C" with --at 4°C--

Column 11, lines 34-35, replace "NaC" with -- NaCl --

Column 12, line 47, replace "NaCI" with --NaCl--

Column 14, line 35, replace "GQFFTP" with --GQFFTP--

Column 14, line 35, replace "LDPACGSGGFL" with --LDPACGSGGFL--

UNITED STATES PATENT AND TRADEMARK OFFICE
CERTIFICATE OF CORRECTION

PATENT NO. : 5,824,529
DATED : October 20, 1998
INVENTOR(S) : Chang, et al.

It is certified that error appears in the above-identified patent and that said Letters Patent is hereby corrected as shown below:

Column 14, line 42, replace "DAILTNPPF" with --DAILTNPPF--

Column 14, line 55, replace "pA1I17" with --pAII17--

Column 3, line 2, replace "abscence" with --absence--

Column 13, line 43, replace "PUC19PshAI" with --pUC19PshAI--

Column 13, line 61, replace "transfered" with --transferred--

Column 16, line 27, replace "NEBlot™" with --NEBlot®--

Column 16, line 28, replace "Phototope™" with --Phototope®--

Column 18, lines 1-2, replace "Circumvent™" with --Circumvent®--

Column 18, line 13, replace "Vent™" with --Vent®--

Column 18, line 21, replace "Vent™" with --Vent®--

Column 18, line 26, replace "Circumvent™" with --Circumvent®--

UNITED STATES PATENT AND TRADEMARK OFFICE
CERTIFICATE OF CORRECTION

PATENT NO. : 5,824,529
DATED : October 20, 1998
INVENTOR(S) : Chang, et al.

It is certified that error appears in the above-identified patent and that said Letters Patent is hereby corrected as shown below:

Column 18, line 56, replace "compatable" with --compatible--

Column 19, line 13, replace "Puc19PshAI" with --pUC19PshaAI--

Column 20, line 1, replace "Vent™" with --Vent®--

Column 20, line 9, replace "Vent™" with --Vent®--

Column 15, line 58, replace "or" with --orf--

Column 17, line 18, replace "GMG" with --GAAG--

Column 19, line 38, replace "GTMTTMT" with --GTAATTAAT--

Column 19, line 44, replace "GTAGMTT" with --GTAGAATT--

Signed and Sealed this

Fourth Day of May, 1999

*Attest:*

Q. TODD DICKINSON

*Attesting Officer*  *Acting Commissioner of Patents and Trademarks*